United States Patent [19]

Smith et al.

[11] 4,001,340
[45] Jan. 4, 1977

[54] HYDROLYSIS OF HALOAROMATIC COMPOUNDS

[75] Inventors: William E. Smith, Midland; Edmund H. Sommerfield, Bay City, both of Mich.

[73] Assignee: The Dow Chemical Company, Midland, Mich.

[22] Filed: Sept. 25, 1975

[21] Appl. No.: 616,728

[52] U.S. Cl. .............................. 260/620; 260/629
[51] Int. Cl.² ...................................... C07C 37/02
[58] Field of Search ........................... 260/620, 629

[56] References Cited

UNITED STATES PATENTS

| | | | |
|---|---|---|---|
| 1,959,283 | 5/1934 | Britton | 260/629 |
| 2,126,648 | 8/1938 | Lofton et al. | 260/629 |
| 3,440,290 | 4/1969 | Widiger | 260/629 |
| 3,536,767 | 10/1970 | Sommerfield | 260/629 |
| 3,778,481 | 12/1973 | Beller et al. | 260/629 |
| 3,904,695 | 9/1975 | Hendrickx et al. | 260/629 |

OTHER PUBLICATIONS

"Industrial and Engineering Chemistry," 20 (2), pp. 114–124 (1928).
Meharg et al., "J.A.C.S.," vol. 54, pp. 2990–2992 (1932).

*Primary Examiner*—Norman Morgenstern
*Attorney, Agent, or Firm*—Carol Jean Cavender

[57] ABSTRACT

The temperature requirements for hydrolysis of a non-phenolic haloaromatic compound by a concentrated aqueous hydroxide solution are lowered by the presence of a phenolic compound.

14 Claims, No Drawings

HYDROLYSIS OF HALOAROMATIC COMPOUNDS

BACKGROUND OF THE INVENTION

The established technique for hydrolyzing unactivated haloaromatic compounds to phenolic compounds is to contact the haloaromatic compounds with dilute aqueous solutions of alkali metal hydroxides at temperatures under about 400° C. Copper catalysts are used to increase the yield of unrearranged products. The potential value of using more concentrated hydroxide solutions has been recognized (U.S. Pat. No. 3,440,290), but even studies which explored the effect of base concentration on the aqueous hydrolysis of non-phenolic haloaromatic compounds were limited to 36% caustic. (*Ind. Eng. Chem.*, 38 254–261 (1946); *J. Am. Chem. Soc.*, 79 1458–1462 (1957).) More concentrated hydroxide solutions or lower temperatures can be used for hydrolysis of halophenols than for non-phenolic haloaromatic compounds. Likewise, alcohol or glycol solvents are known to permit the use of stronger bases or lower temperatures for the hydrolysis of haloaromatic compounds. (See U.S. Pat. Nos. 2,126,648; 2,644,015.) The use of concentrated aqueous base in the hydrolysis requires higher temperatures than are necessary with dilute bases, and these conditions result in an increase of dimeric products such as diaryl phenols and diaryl ethers. (See German Pat. No. 1,930,341.)

SUMMARY OF THE INVENTION

It has now been discovered that the hydrolysis of non-phenolic haloaromatic compounds can be achieved with concentrated aqueous base solutions at temperatures comparable to those necessary to achieve the hydrolysis with dilute aqueous base. Hydrolysis under these strong base, low temperature conditions requires the presence of a phenolic compound. If the phenolic compound is one that is expected to be a product of the hydrolysis, one avoids problems of separation and purification that occur when alcoholic solvents are used. The required phenolic compound may be directly added to the reaction mixture or it may be produced in the reaction mixture by starting the reaction under conditions of sufficiently dilute base or high temperatures.

DETAILED DESCRIPTION OF THE INVENTION

In particular, it has been found that haloaromatic compounds selected from the group consisting of halotoluenes, halobiphenyls, and dihalobenzenes can by hydrolyzed at temperatures of 250°–330° C at autogeneous pressures with 50–100% aqueous alkali metal hydroxide solutions, when a phenolic compound is present. When a copper catalyst is used, there is a very high rate of conversion to unrearranged product and very little coupling to produce ethers or other dimeric products.

Suitable haloaromatic compounds include the o-m-, and p-chloro- and bromotoluenes, the o-, m-, and p-chloro and bromo-biphenyls, the o-, m-, and p-dichloro- and dibromobenzenes and the like.

The term "hydrolysis" as herein used includes the metathetical reaction between hydroxide and haloaromatic compound as well as the reaction between water and the haloaromatic compound. In the hydrolysis of the invention the aqueous hydroxide solution should be at least 50% hydroxide by weight. The mole ratio of hydroxide to haloaromatic compound is not a limiting factor in this invention, but practicality dictates a preferable range of about 2:1 to 10:1.

Under these conditions of strong base and low temperature the hydrolysis of the haloaromatic compounds takes place in the presence of phenolic compounds including but not limited to phenol, arylphenols, alkylphenols, halophenols, resorcinol and other polyhydric phenols. The ratio of phenolic compound to haloaromatic reactant should be at least 0.3:1.

The reaction is preferably performed in the presence of an effective amount of copper catalyst such as copper metal, copper oxides, or copper salts.

SPECIFIC EMBODIMENT OF THE INVENTION

EXAMPLE 1

A mixture of 74.0 g of 2-chlorobiphenyl, 109.9 g of 50% aqueous sodium hydroxide, 58.9 g phenol and a catalytic amount of cuprous oxide was heated to 300° C for 1 hour and cooled. Analysis showed a 56.6% conversion of the 2-chlorobiphenyl to phenylphenols with an ortho to meta ratio greater than 100 to 1. Tables I and II give more examples with varying conditions.

TABLE I

| Examples | 2 | 3 | 4 | 5 | 6 | 7 |
|---|---|---|---|---|---|---|
| Moles $\frac{\phi OH^1}{Cl\phi\phi}$ | 0 | 0 | 0.3 | 1.00 | 1.6 | 1.75 |
| Moles $\frac{NaOH}{Cl\phi\phi}$ | 3.5 | 2.5 | 2.24 | 7.04 | 3.5 | 7.04 |
| NaOH conc. % | 50 | 50 | 73 | >90 | 50 | >90 |
| Temp. °C | 275 | 300 | 300 | 275–300 | 275 | 275–290 |
| Time min. | 60 | 60 | 45 | 160 | 60 | 180 |
| % Conversion | 0 | 0 | 94.3 | 91.8 | 57 | 93.1 |
| OPP/MPP[2] | — | — | >68 | 2.47 | >100 | 5.2 |

TABLE II

| Examples | 8 | 9 | 10 | 11 |
|---|---|---|---|---|
| Moles $\frac{\phi OH}{Cl\phi\phi}$ | 0.6 | 0.6 | 0.6 | 0.6[3] |
| Moles $\frac{NaOH}{Cl\phi\phi}$ | 2.5 | 2.5 | 2.5 | 2.5 |
| NaOH conc. % | 50 | 50 | 50 | 50 |
| Temp. °C | 300 | 300 | 300 | 300 |
| Time min. | 60 | 60 | 60 | 60 |
| Catalyst | $Cu_2O$ | CuO | Cu | $Cu_2O$ |
| % Conversion | 93.3 | 99.1 | 55.7 | 99.9 |

[1]In these tables $\phi OH$ is used to mean a phenol and $Cl\phi\phi$, chlorobiphenyl.
[2]OPP and MPP mean ortho-phenylphenol and meta-phenyl-phenol, respectively.
[3]Phenylphenol was used as the phenol.

We claim:

1. In the process of hydrolyzing a non-phenolic haloaromatic compound selected from the group consisting of halotoluenes, halobiphenyls, and dihalobenzenes of the group consisting of the o-, m-, and p-chloro- and bromotoluenes, the o-, m-, and p-chloro and bromo-biphenyls, the o-, m-, and p-dichloro- and dibromobenzenes to produce the corresponding hydroxy aromatic compounds wherein the hydrolysis is effected by reaction of the haloaromatic compound with an alkali metal hydroxide, the improvement comprising conducting the reaction at a temperature of about 250–330° C, in the presence of a phenolic compound, and with a 50–100% aqueous alkali metal hydroxide solution.

2. The process of claim 1 wherein the haloaromatic compound and the hydroxide are contacted in the presence of a copper catalyst.

3. The process of claim 2 wherein the haloaromatic compound is a halotoluene.

4. The process of claim 3 wherein the halotoluene is chlorotoluene.

5. The process of claim 2 wherein the haloaromatic compound is a halobiphenyl.

6. The process of claim 5 wherein the halobiphenyl is chlorobiphenyl.

7. The process of claim 6 wherein the chlorobiphenyl is para-chlorobiphenyl.

8. The process of claim 6 wherein the chlorobiphenyl is ortho-chlorobiphenyl.

9. The process of claim 2 wherein the haloaromatic compound is a dihalobenzene.

10. The process of claim 9 wherein the dihalobenzene is dichlorobenzene.

11. The process of claim 1 wherein the phenolic compound is selected from the group consisting of phenol, arylphenols, alkylphenols, halophenols, resorcinol, and polyhydric phenols.

12. The process of claim 1 wherein the haloaromatic compound is a halobiphenyl and the phenolic compound is an arylphenol.

13. The process of claim 12 wherein the halobiphenyl is chlorobiphenyl and the arylphenol is a phenylphenol.

14. The process of claim 1 wherein the haloaromatic compound is chlorobiphenyl and the phenolic compound is phenol.

* * * * *